: 4,086,077
: Apr. 25, 1978

United States Patent [19]
Doyle, Jr.

[54] COMBATING UNWANTED VEGETATION WITH 1,3,4-THIADIAZOLYLUREAS

[75] Inventor: William C. Doyle, Jr., Leawood, Kans.

[73] Assignee: Gulf Research & Development Company, Pittsburgh, Pa.

[21] Appl. No.: 626,587

[22] Filed: Oct. 28, 1975

Related U.S. Application Data

[63] Continuation of Ser. No. 29,671, Apr. 17, 1970, abandoned.

[51] Int. Cl.$^2$ .............................................. A01N 9/12
[52] U.S. Cl. ................................. 71/90; 260/306.8 D
[58] Field of Search ............................................ 71/90

[56] References Cited

U.S. PATENT DOCUMENTS 3,673,203   6/1972   Miller .......................... 260/306.8 D

OTHER PUBLICATIONS

Kubo et al. "Herbicidal Activity of 1,3,4-Thiadiazole,-Derivatives," J. Agr. Food Chem. vol. 18, No. 1, 1970.

Primary Examiner—Catherine L. Mills
Attorney, Agent, or Firm—Carl A. Cline

[57] ABSTRACT

Undesired vegetation, including crabgrass, Johnson grass and pigweed are effectively controlled in cotton, corn and peanuts in the warm temperate zones by application of an effective amount of 1,3-dimethyl-1-(5-tert-.butyl-1,3,4-thiadiazol-2-yl)urea or the corresponding 1-ethyl-3-methyl compound to the locus of the weeds. A particularly desirable procedure is the use of one of the new herbicides in combination with alachlor to give very broad spectrum weed control, including such noxious weeds as nutsedge.

1 Claim, No Drawings

COMBATING UNWANTED VEGETATION WITH 1,3,4-THIADIAZOLYLUREAS

This is a continuation of U.S. Pat. Application Ser. No. 29,671 filed Apr. 17, 1970 now abandoned.

DESCRIPTION OF THE INVENTION

It has been recently proposed to use certain derivatives of 1,3,4-thiadiazole as selective herbicides. Among these are the thiadiazole ureas of the following general structure formula:

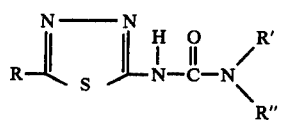

One such compound is 3-methyl-1-(t-tert.-butyl-1,3,4-thiadiazol-2-yl)urea. This compound shows considerable phytotoxic activity against several plant species but is deficient with respect to its ability to control weeds of the legume type, wild buckwheat and weeds of the grassy type such as shattercane and downy brome. It has been discovered, according to this invention, however, that a compound which differs by only a methyl or ethyl substituent in 1- position on the urea structure is superior with respect to the number of plant species which it will control and at the same time is relatively safe to use on crops such as peanuts, corn and sugar cane, particularly in warm temperate and semi-tropical agriculture. The synthesis of the herbicides and use in weed control are discussed below.

METHOD OF PREPARATION

Preparation of 2-tert.butyl-5-methylamino-1,3,4-thiadiazole

To a solution of 91.6 g of 4-methylthiosemicarbazide and 102.3 g of pivalic acid in 400 ml of dioxane at 90° is added slowly 160.5 g of phosphorus oxychloride at such a rate that the reaction temperature is maintained at 85°–90° C. without external heating. When the addition is complete, the mixture is heated at 85°–90° C until HCl evolution ceases (several hours), is cooled and the supernatant liquid decanted from the solid mass in the flask. The mass is broken up, slurried with 700 ml of water and made basic (pH 8–9) by the slow addition of sodium hydroxide pellets. The resulting precipitate is filtered, washed with water, air dried and recrystallized from hexane to give 119.4 g (80% yield) of 2-tert.butyl-5-methylamino-1,3,4-thiadiazole, m.p. 79°–81°.

Preparation of 1,3-dimethyl-1-(t-tert.butyl-1,3,4-thiadiazol-2-yl)urea

To a stirred solution of 486.5 g (2.85 mols) of 2-methyl-amino-5-tert.butyl-1,3,4-thiadiazole in 1700 ml of dioxane is added dropwise 162 g (2.85 mols) of methyl isocyanate over a period of about one hour, during which time the temperature rises to 50°–55°. After stirring an additional 1–2 hours, the slurry is chilled in ice, filtered and the solid is washed with hexane to give 467 g of 1,3-dimethyl-1-(t-tert.butyl-1,3,4-thiadiazol-2-yl)urea, m.p. 162°–4°.

Analysis calcd. for $C_9H_{16}N_4OS$: C, 47.34; H, 7.05; N, 24.54 Found: C, 47.65; H, 6.80; N, 24.57

Preparation of 1-ethyl-1-(5-tert.butyl-1,3,4-thiadiazol-2-yl)-3-methyl urea

A solution of 9.25 g of 2-tert.butyl-5-ethylamino-1,3,4-thiadiazole and 3.5 g of methyl isocyanate is heated several hours on the steam bath and poured into water to give 1-ethyl-1-(5-tert.butyl-1,3,4-thiadiazol-2-yl)-3-methylurea, m.p. 112°.

Analysis calcd. for: $C_{10}H_{18}N_4OS$: C, 49.56; H, 7.49; N, 23.12 Found: C, 49.88; H, 7.46; N, 22.63

Combating Unwanted Vegetation

The novel herbicides are effective when used both post- and pre-emergently. There is described below an illustrative procedure for herbicidal use of the compounds under controlled conditions in the greenhouse so as to obtain data on phytotoxic activity and selectivity.

(1) Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound was to be tested were planted in ten-centimeter pots in a greenhouse. Ten to eighteen days after emergence of the plants, three pots of each species were sprayed with an aqueous dispersion of the active compound prepared as described above, at a rate of 5.6 kilograms of active compound per hectare and at a spray volume of 561 liters per hectare. Approximately one week after the spray application the plants were observed and the results rated according to the following schedule.

DEGREE OF EFFECT

0 = no effect
1 = slight effect
2 = moderate effect
3 = severe effect
4 = maximum effect (all plants died)

The same rating schedule was employed to judge pre-emergent results obtained according to the procedure below.

(2) Pre-Emergent Use

A solution of each active compound was prepared by dissolving 290 mg of the compound to be tested in 200 ml of acetone. Disposable expanded polystyrene trays about 6.4 centimeters deep and about .09 square meter in area were prepared and seeded with the acetone solution at the rate of 11.2 kilograms of active chemical per hectare of sprayed area and were then covered with about 6.4 millimeter of soil. One group of trays, which had been seeded with alfalfa, brome, flax, oats, radishes and sugar beets were held at 24° C. day temperature; another set of trays seeded with corn, coxcomb, cotton, crabgrass, millet and soybeans was held at 29° C. Twenty-one days after seeding and treatment the plantings were examined and herbicidal effect was rated according to the above schedule.

Both post-emergent and pre-emergent results are set forth in the following table.

|  | 1,3-Dimethyl-1-(5-tert.butyl-1,3,4-thiadiazol-2-yl)urea | | 1-Ethyl-1-(5-tert.butyl-1,3,4-thiadiazol-2-yl)-3-methylurea | |
|---|---|---|---|---|
|  | POST | PRE | POST | PRE |
| Crabgrass |  | 4 |  | 4 |
| Coxcomb |  | 4 |  | 4 |
| Brome |  | 4 |  | 4 |
| Millet | 4 | 4 | 4 | 4 |
| Soybean | 4 | 4 | 4 | 4 |
| Cotton | 4 | 4 | 4 | 4 |
| Alfalfa | 4 | 4 | 4 | 4 |
| Oats | 4 | 4 | 4 | 4 |
| Corn | 4 | 3 | 1 | 3 |
| Flax | 4 | 4 | 4 | 4 |
| Radish | 4 | 4 | 4 | 4 |
| Sugar Beet | 4 | 4 | 4 | 4 |
| Wheat | 4 |  | 4 |  |
| Grain Sorghum | 4 |  | 3 |  |
| Tomato | 4 |  | 4 |  |

In further experiments the rate of application of each herbicide was decreased so as to make more apparent its pattern of herbicidal selectivity. Results are tabulated below:

| PRE-EMERGENT USE OF 1-Ethyl-1-(5-tert.butyl-1,3,4-thiadiazol-2-yl)-3-methylurea and 1,3-Dimethyl-1-(5-tert.butyl-1,3,4-thiadiazol-2-yl)urea | | | | | |
|---|---|---|---|---|---|
|  | 5.6 kg/hectare | | 2.24 kg/hectare | | 1.12 kg/hectare | |
| 1-sub-stituent | —CH₃ | —C₂H₅ | —CH₃ | —C₂H₅ | —CH₃ | —C₂H₅ |
| Crabgrass | 4 | 4 | 3 | 4 | 3 | 4 |
| Coxcomb | 4 | 4 | 4 | 4 | 4 | 4 |
| Brome | 4 | 4 | 3 | 4 | 2 | 4 |
| Millet | 4 | 4 | 4 | 4 | 4 | 4 |
| Soybean | 3 | 4 | 3 | 4 | 3 | 4 |
| Cotton | 2 | 3 | 1 | 1 | 1 | 0 |
| Alfalfa | 4 | 4 | 4 | 4 | 4 | 4 |
| Oats | 4 | 4 | 4 | 4 | 3 | 3 |
| Corn | 2 | 2 | 2 | 1 | 1 | 1 |
| Flax | 4 | 4 | 4 | 4 | 4 | 4 |
| Radish | 4 | 4 | 4 | 4 | 4 | 4 |
| Sugar Beet | 4 | 4 | 4 | 4 | 4 | 4 |

| POST-EMERGENT USE OF 1-Ethyl-1-(5-tert.butyl-1,3,4-thiadiazol-2-yl)-3-methylurea and 1,3-Dimethyl-1-(5-tert.butyl-1,3,4-thiadiazol-2-yl)urea | | | | |
|---|---|---|---|---|
|  | RATE 2.24 kg/hectare | | RATE 1.12 kg/hectare | |
| 1-Substituent | —CH₃ | —C₂H₅ | —CH₃ | —C₂H₅ |
| Millet | 4 | 4 | 4 | 4 |
| Soybean | 4 | 4 | 4 | 3 |
| Cotton | 4 | 4 | 4 | 4 |
| Alfalfa | 4 | 4 | 4 | 4 |
| Oats | 4 | 4 | 4 | 4 |
| Corn | 4 | 1 | 3 | 1 |
| Flax | 4 | 1 | 4 | 1 |
| Radish | 4 | 4 | 4 | 3 |
| Sugar Beet | 4 | 4 | 4 | 4 |
| Wheat | 4 | 4 | 4 | 2 |
| Grain Sorghum | 4 | 2 | 3 | 1 |
| Tomato | 4 | 4 | 4 | 4 |

So as to demonstrate the difference between the novel herbicides of this invention and the prior art compound which differs in the absence of a methyl or ethyl substituent at the 1- position, comparative tests were made between these herbicides and a common commercial herbicide (diuron) at pre-emergent application rates of both 1.12 kg. per hectare and 0.56 kg. per hectare against 23 plant species. The experiments were carried out in essentially the same manner as described above. The 1-ethyl-substituted compound was shown to be safe on both peanuts and cotton at the 1.12 kg. per hectare rate of application and was not tested at a lower rate, since this would merely reduce weed control without benefit to the crop. The 1-methyl-substituted compound was shown to be more active and was completely safe on both peanuts and cotton only at the lower rate of application. The test data are tabulated below.

PRE-EMERGENT TEST COMPARISON OF NOVEL HERBICIDES WITH PRIOR ART COMPOUNDS

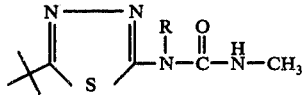

| Plant Species | 1.12 kg/hectare R-Substituent | | | Di-uron | 0.56 kg/hectare R-Substituent | | Di-uron |
|---|---|---|---|---|---|---|---|
|  | —C₂H₅ | —H | —CH₃ |  | —H | —CH₃ |  |
| Pigweed | 4 | 4 | 4 | 4 | 4 | 4 | 4 |
| Lambs-quarters | 4 | 4 | 4 | 4 | 4 | 4 | 4 |
| Wild Buckwheat | 4 | 2 | 4 | 4 | 0 | 4 | 3 |
| Tomato | 3 | 3 | 4 | 4 | 0 | 4 | 4 |
| Morning Glory | 2 | 1 | 4 | 1 | 0 | 1 | 1 |
| Cotton | 0 | 0 | 4 | 0 | 0 | 0 | 0 |
| Alfalfa | 4 | 4 | 4 | 4 | 4 | 4 | 4 |
| Wild Mustard | 4 | 4 | 4 | 4 | 4 | 4 | 4 |
| Sugar Beet | 4 | 4 | 4 | 3 | 4 | 4 | 4 |
| Peanut | 0 | 0 | 1 | 0 | 0 | 0 | 0 |
| Soybean | 2 | 2 | 4 | 1 | 0 | 2 | 0 |
| Crabgrass | 4 | 4 | 4 | 4 | 4 | 4 | 4 |
| Green Foxtail | 4 | 4 | 4 | 4 | 3 | 4 | 2 |
| Rice | 4 | 4 | 4 | 3 | 3 | 4 | 4 |
| Wheat | 4 | 4 | 4 | 1 | 1 | 4 | 0 |
| Barnyard Grass | 2 | 3 | 4 | 4 | 2 | 3 | 2 |
| Nutsedge | 0 | 0 | 0 | 0 | 0 | 0 | 0 |
| Downy Brome | 1 | 0 | 4 | 0 | 0 | 3 | 0 |
| Giant Foxtail | 3 | 1 | 4 | 1 | 0 | 4 | 0 |
| Wild Oats | 4 | 3 | 4 | 1 | 1 | 3 | 0 |
| Shattercane | 1 | 0 | 4 | 0 | 0 | 2 | 0 |
| Grain Sorghum | 1 | 0 | 3 | 0 | 0 | 2 | 0 |
| Corn | 1 | 0 | 2 | 0 | 0 | 1 | 0 |

0 = no injury
4 - complete kill

The effectiveness of the new thiadiazolyl urea herbicides on such weeds as wild buckwheat, giant foxtail and wild oats is evident in the results of these herbicide tests.

A particularly advantageous method of use of the new dimethylurea herbicide in peanut culture is in combination with the commercial herbicide alachlor, the chemical name of which is 2-chloro-2',6'-diethyl-N-(methoxymethyl)acetanilide. Results obtained in pre-emergent use of the combination of two herbicides are tabulated below. It will be seen that with this combination it is feasible to obtain complete control of a number of the most troublesome weeds in peanuts and corn fields, even including nutsedge, without injury to the peanuts. It is preferred to use one part of the thiadiazolyl 1,3-dimethylurea herbicide in combination with from two to four parts of the other herbicide.

HERBICIDE COMBINATIONS

| Rate (kg/hectare) 2-Chloro-2',6'-diethyl-N-(methoxymethyl) acetanilide (alachlor) | Rate (kg/hectare) 1,3-Dimethyl-1-(5-*tert.*butyl-1,3,4-thiadiazol-2-yl)urea | Pig-weed | Cot-ton | Morn-ing Glory | Ses-ban-ia | Crab-grass | Nut-sedge | Pea-nut | Cock-le-burr | John-son Grass | Yel-low Fox-tail | Barn-yard Grass | Corn |
|---|---|---|---|---|---|---|---|---|---|---|---|---|---|
| 3.36 | 0    | 4 | 0 | 0 | 1 | 4 | 3 | 0 | 0 | 4 | 4 | 4 | 1 |
| 2.24 | 0    | 4 | 0 | 0 | 0 | 4 | 2 | 0 | 0 | 4 | 4 | 4 | 0 |
| 3.36 | 1.12 | 4 | 4 | 4 | 4 | 4 | 4 | 0 | 4 | 4 | 4 | 4 | 1 |
| 1.68 | 0.56 | 4 | 4 | 3 | 4 | 4 | 2 | 0 | 4 | 4 | 4 | 4 | 1 |
| 3.36 | 0.56 | 4 | 4 | 3 | 4 | 4 | 2 | 0 | 3 | 4 | 4 | 4 | 0 |
| 2.24 | 1.12 | 4 | 4 | 4 | 4 | 4 | 3 | 0 | 4 | 4 | 4 | 4 | 1 |

What is claimed is:

1. The method of combating unwanted vegetation by applying to the locus of the vegetation an effective amount of 1,3-dimethyl-1-(5-*tert.*butyl-1,3,4-thiadiazol-2-yl)urea.

* * * * *